United States Patent [19]

Colwell

[11] Patent Number: 5,496,555
[45] Date of Patent: Mar. 5, 1996

[54] PERSONAL CLEANING COMPOSITION

[75] Inventor: Dennis Colwell, East Windsor, N.J.

[73] Assignee: Colgate-Palmolive Company, Piscataway, N.J.

[21] Appl. No.: 278,444

[22] Filed: Jul. 21, 1994

Related U.S. Application Data

[63] Continuation-in-part of Ser. No. 48,983, Apr. 16, 1993, abandoned.

[51] Int. Cl.$^6$ .................................................... A61K 7/48
[52] U.S. Cl. .......................... 424/405; 424/400; 424/401
[58] Field of Search .................................. 424/401, 405, 424/400

[56] References Cited

U.S. PATENT DOCUMENTS 5,139,781  8/1992  Birtwistle et al. ..................... 424/401

*Primary Examiner*—Thurman K. Page
*Assistant Examiner*—C. Azpuru
*Attorney, Agent, or Firm*—Robert C. Sullivan; Martin B. Barancik

[57]  ABSTRACT

A cleansing composition useful for the skin or hair comprising a surfactant, a green colorant, a dicarbanalide, and a color stabilzing system which is comprised of a sorbitan like compound and a polyethylene glycol.

13 Claims, No Drawings

PERSONAL CLEANING COMPOSITION

BACKGROUND OF THE INVENTION

This application is a continuation-in-part application of U.S. Ser. No. 08/048,083, filed on Apr. 16, 1993 now abandoned.

Personal cleanser compositions are being constantly improved. For many years such compositions have been carriers for bacterial inhibiting or destroying materials commonly known as bacteriostats or bacterocides. These materials are dispersed throughout the personal cleansing composition and are deposited on the body at the time of application of the cleansing composition. For the bacteriostat or bacteriocide to work effectively it must be highly and evenly dispersed throughout the cleansing compostion at a significant level. Many of these antibacterial agents are organic while the cleansing compositions are often aqueous in nature. This leads to difficulties in obtaining adequate dispersion. Such difficulties are sometimes addressed by the addition of a solubilizing agent which aids the dispersion of the antibacterial material through the cleansing composition. Such solubilization agent should achieve these results without significantly affecting the desired properties of the cleansing composition.

In attempting to solubilize a certain antibacterial agent in a cleansing composition through use of solubilizing materials, certain problems were encountered, specifically in the color stability of the composition. This problem was overcome in a novel and unexpected manner by utilizing a blend of solubilizing materials. Each of these materials alone caused unacceptable color destabilization of the composition.

SUMMARY OF THE INVENTION

In accordance with the invention, there is a cleansing composition useful for the skin or hair comprising.
a. a surfactant,
b. a green colorant,
c. a compound of the formula

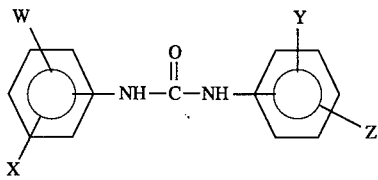

wherein W, X, Y and Z are the same or different and are halogen or hydrogen,
d. a composition of the formula

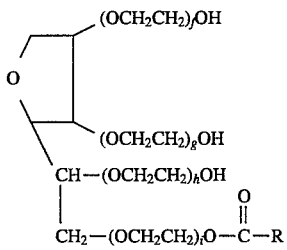

wherein f, g, h and i are the same or different and their sum total average is an integer of about 16 to 24 and R is alkyl of an average number of carbon atoms of about 9 to 13, and
e. a composition of the formula

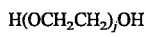

wherein j is an integer and has an average value of about 8 to 16, and wherein the ratio of d to e is such that the color of the composition remains an acceptable green to blue.

DETAILED DESCRIPTION OF THE INVENTION

Any cleansing composition for the skin or hair and having a surfactant is a part of this invention. The surfactant can be a traditional soap, that is the alkali metal or an amine salt of a fatty carboxylic acid or an anionic, zwitterionic, cationic or nonionic surfactant. Examples of such surfactants include and are illustratively exemplified in U.S. Pat. No. 5,139,781, column 5, line 35, to column 11, line 33, incorporated by reference in its totality into this specification. A mixture of surfactants can be employed. The quantity of surfactant employed in the liquid or solid composition is not unduly significant and can vary from about 1 to about 99 wt %, preferably a minimum of about 3 wt % or 5 wt % is generally used. Because of various other materials which can be present in the composition such as free fatty acids, emollients, moisturizers, skin conditioners and the like as well as moisture in general, the maximum quantity of such surfactant does not generally rise about the level of about 90 to 95 wt %.

The composition can take the form of a liquid such as a liquid soap, shampoo, bubble, shower gel and the like or a solid form such as a bar which can illustratively be a soap, combar or syndet composition.

When utilizing a soap it is preferably a tallowate, cocoate or palm kernalate type, usually in the sodium salt form. When more than one soap is present, the ratio of tallow fatty acid to coconut oil fatty acid can range from about 40 wt % to about 90 wt % sapionified tallow fatty acid and from about ten to about 60 wt % sapionified coconut oil fatty acid. Such soaps can be "super fatted" as well through the addition of quantities of free fatty acid such as stearic acid, palmitic acid or other long chain fatty acids. Wt % of the acids are from about 1.0 to about 10.0 of the composition.

Other surfactants which may be present in cleansing compositions are alcohol glyceryl sulfonate, long chain carboxy esters of isethionate salts (sodium cocoylisethionate) and the like.

The invention is particularly related to the use of colorant which provides a green color to the cleansing composition. Any colorant which achieves this goal in the composition can be employed. For example green colorants such as D&C Green #8 and/or FD&C Green #3 are preferred colorants in the compositions of this invention. Generally, they are added to the composition as an aqueous dispersion. The quantity of colorant is not unduly significant as long as it imparts the desired color to the composition. Wt % of the colorant of from about 0.0005 to 0.005 of the composition can be readily utilized.

Component c of the claimed composition is an antibacterial agent of the formula.

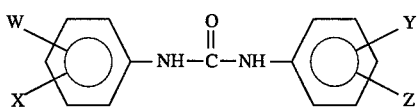

wherein W, X, Y and Z are the same or different and are halogen or hydrogen. Halogen is fluoro, chloro, bromo, or iodo. The preferable halogen are chloro or bromo, most preferably chloro. The most preferable compound of the formula is generically known as triclorcarban or trichlorocarbanilide; CAS number 101-20-2. With respect to the schematic formula above, W is meta chloro, X is para chloro, Y is para' chloro and Z is hydrogen. Wt % of the antibacterial agents are not unduly significant; however, there should generally be enough to provide effective, relatively long lasting antibacterial effect on the skin or hair when such agent is evenly dispersed throughout the cleansing composition. Generally, a minimum of about 0.1 wt % of the agent is usually employed. More agent can be used, the upper limit depending upon such factors as compatibility, irritancy, cost and the like. Generally no more than about 1.0. wt % of the compositon is employed.

Components d and e serve to solubilize the component c. This combination of solubilizing materials is significant since either d or e alone brings about an unacceptable "blueing" of the composition, as aforementioned. Very surprisingly, however, mixtures of these two components at appropriate ratios provide significantly less blueing than either d or e alone.

Component d material sum total of f, g, h and i is preferably 18 to 22, most preferably 20. The alkyl group R, is either branched or normal, preferably normal and has a preferred average value of carbon atoms of ten to twelve, more preferably 11. An example of such a material is Polysorbate 20, CAS Number 9005-64-5 and is commercially available from numerous sources.

Component e has a preferred average value for j of about 10 to 14, most preferably 12 and in that most preferred form is generically known as PEG-12. It is also commercially available from numerous sources.

The mixture of d and e in appropriate quantities maintains the composition color at a desirable level of green to blue over time. The testing procedures include both visual perception and instrumental measurement. Visually, the color is observed at time of bar preparation and after aging for four weeks at 110° F. Instrumental measurement using a Macbeth Series 1500 colorimeter b axis value at both preparation and after aging four weeks at 110° F. is utilized. In tristimulus color measurement, the b axis represents the visual yellow to green perception. The more stable the color, the less change appears between the initial measurement by instrument or visual perception and the aged measurement by instrument or visual perception after four weeks at 110° F. As previously noted, 100% of either d or e brings about an unacceptable blue color change for the composition either instrumentally, visually, or both. Generally on a wt % basis of d and e, a mixture of about 33% to 70% d and about 30% to 67% e brings about acceptable color. Preferred mixtures of d and e are from about 40 wt % to 67 wt % d.

The total quantity of d and e is that amount which brings about the desired solubilization as well as maintaining the acceptable colors and is from about 0.25 to 1.75 wt % of the composition, preferably about 0.5 to 1.25 wt %.

The composition is prepared utilizing common techniques. The antibacterial agent is added to a previously mixed combination of the solubilizing agents heated to a temperature of about 80°–100° C., preferably about 80°–85° C. with moderate agitation. This admixture is then added to the surfactant composition with appropriate mixing means.

Below are comparative examples illustrating the poor color achieved with both 100% d and 100% e. Also presented are examples of the invention demonstrating the results achieved when appropriate ratios of d and e together are used. These examples are intended to be illustrative of the invention and not be limiting of the broad inventive concept.

In the examples below, a composition of about 95 wt % soap and moisture, the soap being a blend of 60 wt % tallow and 40 wt % coconut oil fatty acid salts, was employed. Also present was a fragrance, glycerin, preservatives, titanium dioxide, green colorants D&C #8 and FD&C #3. 0.3 wt % of trichlorocarbanilide was also present. A total of 1.2 wt % of the solubilizers was also present as 100% of either d or e or various blends of d and e. Bars were prepared in each instance. The bars were observed for color immediately after preparation both visually and by use of the b axis of the Macbeth colorimeter. After aging the bars for four weeks at 110° F., the color was once more evaluated both visually and instrumentally. Below are the results:

In the table PEG is PEG 12, an example of an e component and was obtained from Union Carbide.

Tween 20 is an example of the d component (i.e. polysorbate 20) and was obtained from ICI America.

The Δb column represents the change in the instrumental b axis value observed from preparation followed by four weeks aging. The smaller the value the better is the stability.

TABLE 1

| Example | Solubilizer, wt % | Δb | Visual blueing |
|---|---|---|---|
| 1 | 100% PEG 12 | −5.68 | Severe blueing |
| 2 | 100% Tween 20 | −8.69 | Moderate to severe |
| 3 | 66% Tween 20 33% PEG 12 | −4.76 | Moderate |
| 4 | 50% Tween 20 50% PEG 12 | −5.49 | Slight |
| 5 | 50% Tween 20 50% PEG 12 | −4.63 | Slight |
| 6 | 75% Tween 20 25% PEG 12 | −6.77 | Moderate |

As can be observed from the results above, the 100% component d or e provides unacceptable color ageing. Specific blends of the two components provide acceptable color ageing.

I claim:

1. A cleansing composition comprising a. about 1–99 wt % of a surfactant, b. a green colorant in an effective amount to cause green coloration, c. an antibacterial effective, compatible non-irritating amount of a compound of the formula.

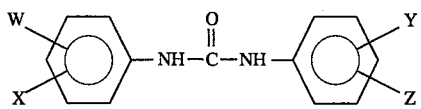

wherein W, X, Y and Z are the same or different and are halogen or hydrogen, d. A component of the formula

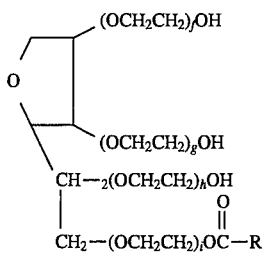

wherein the sum total of f, g, h and i is an integer of average of about 16 to 24 and R is an alkyl of an average number of carbon atoms of about 9 to 13, and e. a component of the formula

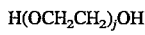

wherein j has an average value of an integer of about 8 to 16 wherein the ratio of d to e is such that the composition color remains stable over time as measured by visual perception and/or the b axis value of a tristimulus colorimeter, d is about 33 to 70 wt % of d and e together and d and e combined are about 0.25 to 1.75 wt % of the composition.

2. The composition in accordance with claim 1 wherein the surfactant is a soap.

3. The composition in accordance with claim 1 wherein W, X, Y and Z are chloro.

4. The composition in accordance with claim 1 wherein W, X and Y are chloro and Z is hydrogen.

5. The composition in accordance with claim 4 wherein W is meta chloro, X is para chloro and Y is para' chloro, trichlorocarban.

6. The composition in accordance with claim 1 wherein d is about 40 to 67 wt % of d and e together.

7. The composition in accordance with claim 2 wherein c is trichlorocarban and d is about 40 to 67 wt % of d and e together.

8. The composition in accordance with claim 5 wherein c is present in from about 0.1 to 1.0 wt %.

9. A cleansing composition comprising a. about 1–99 wt % of a surfactant, b. a green colorant in an effective amount to cause green coloration, c. about 0.1 to 1.0 wt % of a compound of the formula

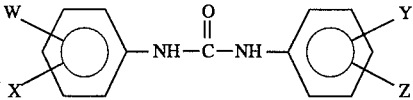

wherein W, X, Y and Z are the same or different and are halogen or hydrogen, d. A composition of the formula

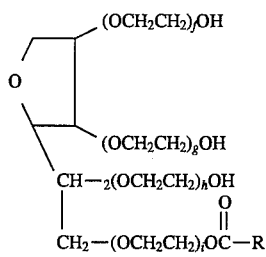

wherein the sum total of f, g, h and i is an integer of average of about 16 to 24 and R is an alkyl of an average number of carbon atoms of about 9 to 13, and e. a composition of the formula

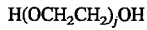

wherein j has an average value of an integer of about 8 to 16 wherein d is about 33 to 70 wt % of d and e and d and e combined are about 0.25 to 1.75 wt % of the composition.

10. The claim in accordance with claim 1 wherein the composition is in bar form.

11. A cleansing composition comprising a. about 1–99 wt % of a surfactant, b. a green colorant in an effective amount to cause green coloration, c. about 0.1 to 1.0 wt % of a compound of the formula

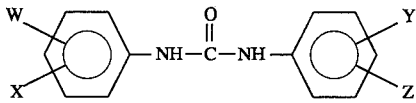

wherein W, X, Y and Z are the same or different and are halogen or hydrogen, d. A component of the formula

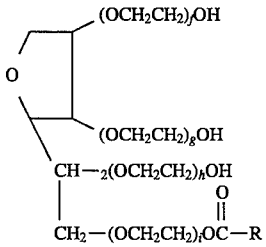

wherein the sum total of f, g, h and i is an integer of average of about 16 to 24 and R is an alkyl of an average number of carbon atoms of about 9 to 13, and e. a component of the formula

wherein j has an average value of an integer of about 8 to 16 wherein the ratio of d to e is such that the composition color remains stable over time as measured by visual perception and/or the b axis value of a tristimulus colorimeter, d is about 33 to 70 wt % of d and e together and d and e combined are about 0.25 to 1.75 wt % of the composition.

12. The claim in accordance with claim 11 wherein c is trichlorocarban.

13. The claim in accordance with claim 12 wherein the composition is in bar form.

* * * * *